United States Patent [19]

Hagi

[11] Patent Number: 5,402,001
[45] Date of Patent: Mar. 28, 1995

[54] METHOD OF CHECKING FOR FOREIGN MATTER ON A SUBSTRATE WITH LIGHT OF MAXIMUM REFLECTIVITY FOR THAT SUBSTRATE

[75] Inventor: Toshio Hagi, Katano, Japan

[73] Assignee: Matsushita Electric Industrial Co., Ltd., Osaka, Japan

[21] Appl. No.: 87,531

[22] Filed: Jul. 8, 1993

[30] Foreign Application Priority Data

Oct. 5, 1992 [JP] Japan .................................. 4-265982

[51] Int. Cl.6 .......................................... G01N 21/88
[52] U.S. Cl. .................... 250/571; 250/572; 250/226; 250/228; 356/430
[58] Field of Search ............... 250/562, 571, 572, 226, 250/223 R, 223 B, 228; 356/237, 338, 430

[56] References Cited

U.S. PATENT DOCUMENTS

| | | | |
|---|---|---|---|
| 4,626,101 | 12/1986 | Ogawa et al. | 356/237 |
| 4,740,708 | 4/1986 | Batchelder | 250/572 |
| 4,768,878 | 9/1988 | Heine et al. | 356/237 |
| 4,823,169 | 4/1989 | Ogura | 356/430 |
| 4,902,131 | 2/1990 | Yamazaki et al. | 356/237 |
| 4,967,095 | 10/1990 | Berger et al. | 250/572 |

FOREIGN PATENT DOCUMENTS 62-223651 10/1987 Japan .
245735 2/1990 Japan .
4113358 4/1992 Japan .

*Primary Examiner*—David C. Nelms
*Assistant Examiner*—Stephone B. Allen
*Attorney, Agent, or Firm*—Stevens, Davis, Miller & Mosher

[57] ABSTRACT

A method and an apparatus for checking and detecting foreign matter on the surface of a semiconductor substrate with high and stable sensitivity, and with high precision. The respective reflectivities at which light of various wavelengths within a wide wavelength range is reflected from each multi-layer thin film substrate are measured, and light of a wavelength at which the light is reflected at a local-maximum reflectivity is selected as monitor light for foreign matter checking with respect to each substrate. The apparatus comprises, as a light source, a light source for generating light within a wide wavelength range and a filter for narrowing the wavelength range of light so as to obtain monitor light which is to be radiated onto a substrate to check foreign matter. Variations in detection sensitivity due to slight variations in the thickness of deposited films on semiconductor substrates can be restrained to thereby realize foreign matter checking with stable sensitivity.

7 Claims, 4 Drawing Sheets 340 nm    350 nm    360 nm 340 nm    350 nm    360 nm

METHOD OF CHECKING FOR FOREIGN MATTER ON A SUBSTRATE WITH LIGHT OF MAXIMUM REFLECTIVITY FOR THAT SUBSTRATE

BACKGROUND OF THE INVENTION

1. Field of the Invention

The present invention relates to foreign matter checking in which particles of foreign matter on a semiconductor substrate are detected.

2. Description of the Related Art

In recent years, as integrated circuit technologies have come to achieve higher and higher levels of circuit integration, the patterns of elements formed on semiconductor substrates have become more and more minute. In these circumstances, when there are any particles of foreign matter on the surface of a semiconductor substrate, a minute pattern cannot be formed properly, resulting in a reduced yield of integrated circuits. Accordingly, it is necessary to check for fine particles of foreign matter on semiconductor substrates, and to control the number, the size and the distribution of such foreign particles.

Hitherto, a system known as a laser scattering system has been employed to detect particles of foreign matter on semiconductor substrates. In this system, a laser beam from a laser source is projected onto the surface of a semiconductor substrate. If there is any foreign particle on the semiconductor substrate, a portion of the laser beam is scattered. Such scattering of the laser beam is detected to check foreign matter on the substrate (see Japanese Patent Unexamined Publication No. 3-225939).

In the conventional system for checking foreign matter by utilizing laser beam scattering, the light source is one that generates light of a single wavelength. As a result, when the substrate subjected to foreign matter checking is a multi-layer thin film substrate having a film of a plurality of layers deposited thereon, light scattered by a foreign particle causes interference, as shown in FIG. 5, and such interference creates some detection sensitivity-reduced regions in the deposited film in which region the capability for measuring the size of foreign particles deteriorates. Moreover, the thickness of films deposited in a semiconductor process may subtly vary among a plurality of thin film semiconductor substrates, thereby causing variations in the sensitivity with which foreign particles on the substrates can be detected.

SUMMARY OF THE INVENTION

An object of the present invention is to provide a foreign matter checking apparatus and a foreign matter checking method that is capable of restraining deterioration and variations in detection sensitivity, and is thus capable of exhibiting stable sensitivity of foreign matter detection.

In a foreign matter checking method according to the present invention, a substrate having a multi-layer thin film formed thereon is subjected to a check as to whether or not there is foreign matter on the surface of the substrate. The respective reflectivities at which light of various wavelengths within a wide wavelength range is reflected from the multi-layer thin film substrate, are measured, and light of a wavelength that has a maximum reflectivity with respect to the multi-layer thin film substrate is selected as monitor light for foreign matter checking. When a plurality of multi-layer thin film substrates are subjected to foreign matter checking, monitor light of a maximum reflectivity is selected with respect to each of the plurality of multi-layer thin film substrates so as to detect or check the foreign matter.

A foreign matter checking apparatus according to the present invention comprises a light source capable of generating light in a wide wavelength range, and the apparatus comprises a wavelength filter for selecting a specific wavelength of monitor light. The wavelength filter narrows the wavelength range of light generated from the light source to a selected wavelength, and the thus obtained light is radiated onto a substrate to be checked. The monitor light and the substrate being checked are moved relative to each other so as to detect any particles of foreign matter on the surface of the substrate.

Foreign matter checking according to the present invention uses, as monitor light, light of a certain wavelength which can be reflected from the multi-layer thin film substrate to be checked at a maximum reflectivity. Since light of a wavelength corresponding to a maximum reflectivity is hardly influenced by slight variations in the thickness of the film deposited on the substrate, it is possible to stabilize the sensitivity with which foreign particles on the substrate are detected.

Since in the invention it is possible to eliminate certain deposited-film thickness regions in which the sensitivity of foreign-particle detection with respect to multi-layer thin film substrates deteriorates, which elimination could not be achieved in a conventional system due to the using of a fixed wavelength, it is possible to achieve substantially the maximum sensitivity in the present invention. Thus, it is possible to perform foreign matter checking with high sensitivity and high precision

DESCRIPTION OF THE PREFERRED EMBODIMENTS

An embodiment of a foreign matter checking apparatus according to the present invention will be described with reference to the accompanying drawings.

Figure 1:
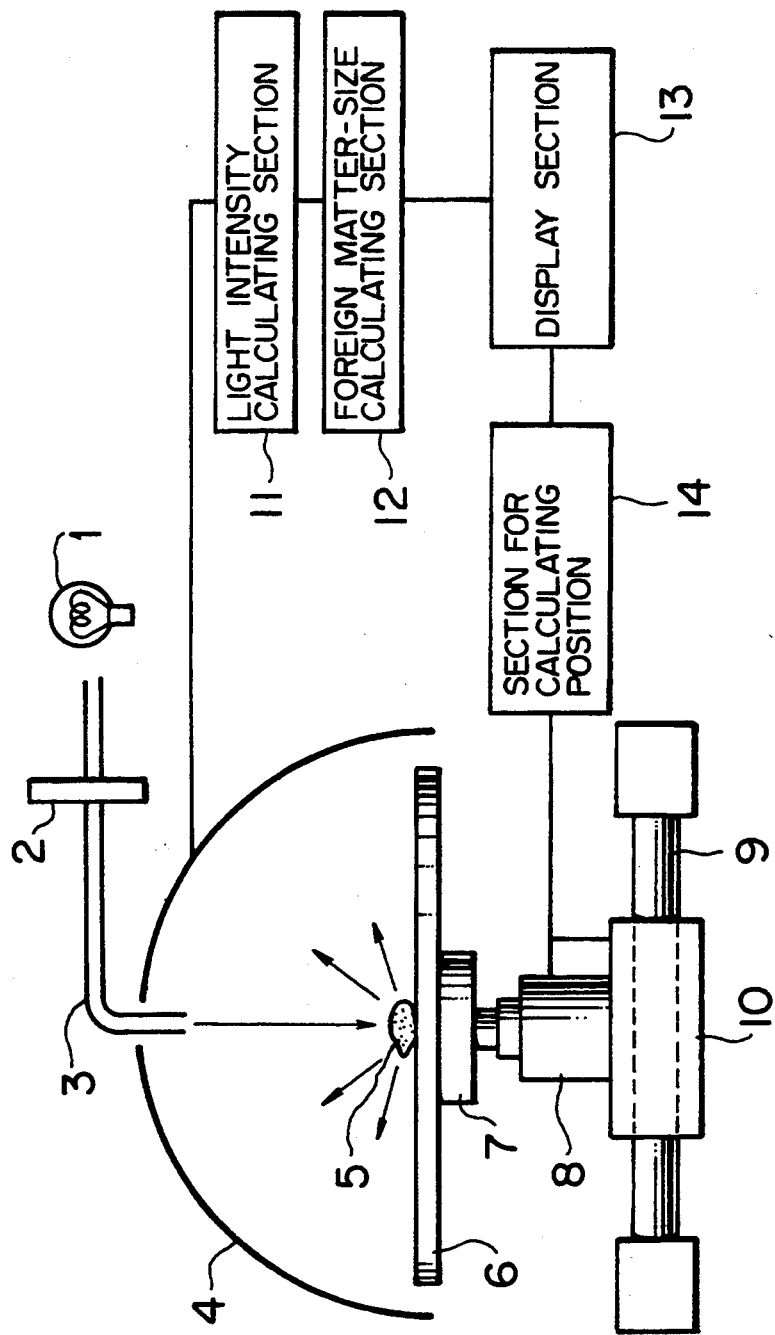
FIG. 1 is a view showing the construction of a foreign matter checking apparatus according to the present invention.

Referring to FIG. 1, schematically showing a foreign matter checking apparatus according to the present invention, the apparatus comprises a light source 1 for generating light within a wide wavelength range, and a wavelength filter 2 for narrowing the wavelength range of light generated from the light source 1 to a specific wavelength range. Light passed through the wavelength filter 2 is radiated onto a wafer 6, serving as a semiconductor substrate being checked, through an optical fiber device 3. The reasons why the wavelength range of light from the wide-wavelength-range light source 1 is narrowed by the wavelength filter 2 (i.e., wavelength selection of monitor light) will be described later with reference to FIG. 2 and FIGS. 3(a) and 3(b).

When there is any particle 5 of foreign matter on the surface of the substrate 6, light radiated thereon scatters. The scattered light is detected by a scattered light detector 4. The size of the foreign matter or particle 5 is determined on the basis of the intensity of the scattered light through both a light intensity calculating section 11 and a section 12 for calculating the size of foreign matter.

Figure 4:
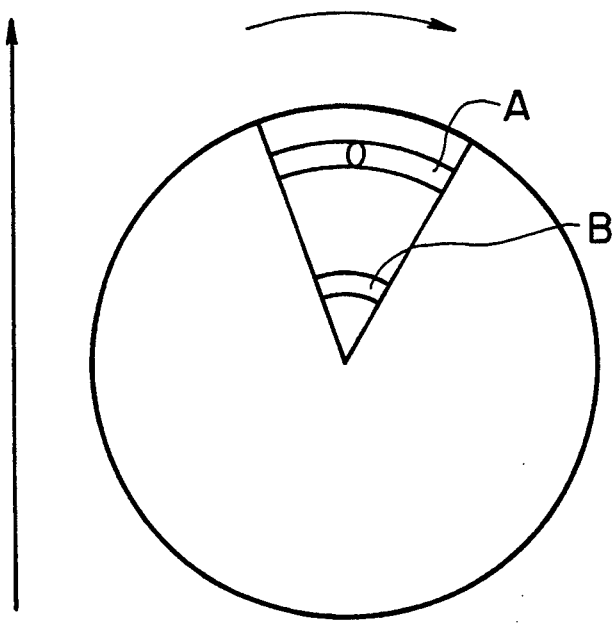
FIG. 4 is a view for illustrating the area that can be scanned per unit time by a spotlight when a semiconductor substrate is being rotated at a fixed speed.
Figure 5:
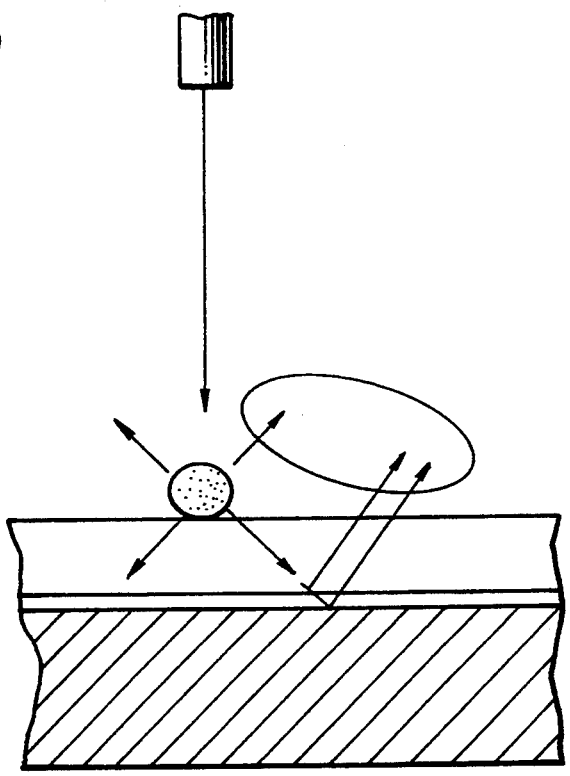
FIG. 5 is a view for illustrating interference caused by light scattered by a particle of foreign matter.

The semiconductor substrate 6 is held by a vacuum chuck 7, and is rotated during a checking operation by a step motor 8. As shown in FIG. 4, if a semiconductor substrate is rotated at a fixed angular velocity, the linear velocity at an outer peripheral position A of the semiconductor substrate is higher than the linear velocity at an inner peripheral position B of the substrate. Therefore, in the apparatus according to the present invention, if the substrate 6 is rotated at a fixed angular speed, the area that can be scanned per unit time by a spot of light emitted from the optical fiber device 3 will apparently vary between a relatively outer peripheral position (such as position A) and a relatively inner peripheral position (such as position B) of the substrate 6. This makes in detection sensitivity differ between outer and inner peripheral positions of the substrate 6.

In order to remove this problem, the apparatus according to the present invention has the motor 8, a shaft 9 and an X-axis drive section 10 which are arranged as follows: the angular speed of rotation of the substrate 6 is increased as the detection position of the substrate 6 is moved from an outer periphery of the substrate to the inner periphery thereof in the direction indicated by arrow X in FIG. 4 in so that detection sensitivity may be constant throughout different positions of detection. This arrangement maintains constant the area scanned per unit time by a spot of monitor light radiated onto the substrate 6, thereby achieving a constant detection sensitivity at any position on the substrate 6.

The substrate 6 is moved in the direction X by a step of approximately 20 $\mu$m per revolution of the substrate 6. This is because the size of a spot of light radiated on the substrate 6 is approximately 20 $\mu$m. Thus, the surface of the substrate 6 is scanned with radiation of light so as to detect the size and the position of foreign particles.

Information on the size and the position of particles of foreign matter detected in this way, is displayed as a batch of data by a display section 13.

The reasons why the foreign matter checking apparatus according to the present invention is adapted to select a specific wavelength of monitor light to be radiated onto the substrate, will be described with reference to FIG. 2 and FIGS. 3(a) and 3(b).

Figure 2:
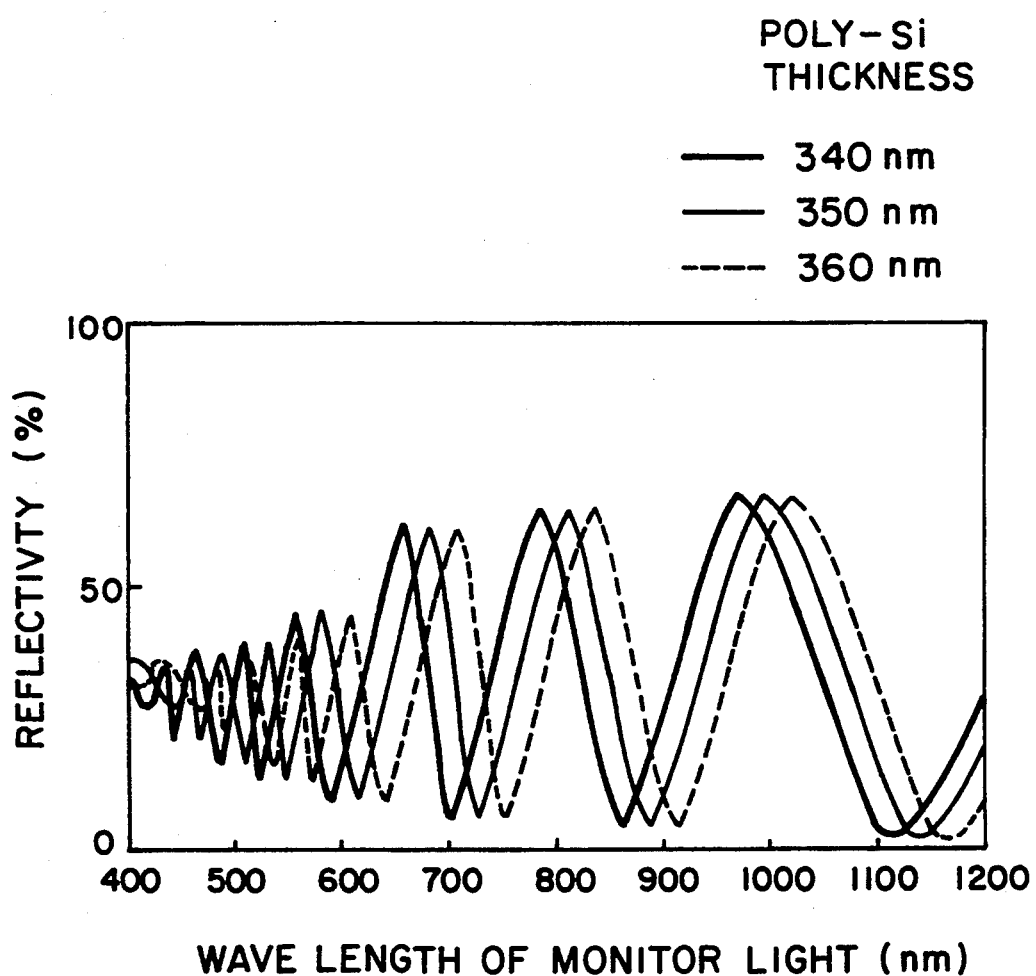
FIG. 2 is a graph showing the relationship between various wavelengths of light and the reflectivities at which light of various wavelengths is reflected from a polysilicon-deposited substrate.

FIG. 2 shows the results of measured changes in the reflectivity of light radiated onto and reflected from a film-deposited silicon (Si) substrate while changing the wavelength of light within the wavelength range from 400 to 1200 nm. Such changes in reflectivity with changes in wavelength were measured by using three film-deposited silicon substrates, each of which had a silicon oxide (SiO$_2$) layer of a thickness of 25 nm deposited on the surface of the silicon substrate, and a polysilicon (poly-Si) layer of a different thickness (i.e., the first substrate had a thickness of 340 nm, the second 350 nm and the third 360 nm) deposited on the silicon oxide layer.

It is understood from FIG. 2 that the reflectivity has local-maximum values at wavelengths of 1000 nm, 820 rum and 680 nm when, as indicated by the thin solid curve in FIG. 2, the substrate is the type having a polysilicon layer with an standard (average) thickness of 350 nm, and that these local-maximum reflectivity values change only very slightly, as compared with other reflectivity values at other wavelengths, even when the thickness of the polysilicon layer changes by $\pm$10 nm. Thus, it is understood that, if light of a wavelength that has a maximum reflectivity is used as monitor light for foreign matter checking, it is possible to minimize the influence of film thicknesses involving interference. Accordingly, the use of light of a wavelength having a maximum reflectivity as monitor light for foreign matter checking is advantageous in that it is possible to minimize variations in detection sensitivity even when slight variations in the film thickness have been caused in a semiconductor process, thereby making it possible to check foreign matter with stable detection sensitivity. In addition, since the reflectivity of the monitor light is relatively high, scattered light has relatively great intensity, thereby making it possible to increase the sensitivity of foreign particle detection.

The results of actual foreign matter checking using monitor light of a wavelength selected in the above manner, will be described with reference to FIGS. 3(a) and 3(b). Shown in these figures are the results of foreign matter checking operations conducted on three different types of film-deposited silicon substrates similar to those described with reference to FIG. 2; each type of substrates had a film comprising a silicon oxide layer with a thickness of 25 nm formed on the silicon substrate, and a polysilicon layer with a different thickness (340 nm, 350 nm or 360 nm) formed on the silicon oxide layer. Substantially the same number of sample particles of a substantially uniform particle size were attached to the surface of each substrate beforehand. FIG. 3(a) shows a case where light of a wavelength of 755 nm was used as the monitor light, and FIG. 3(b) shows another case where light of a wavelength of 820 nm, that is, light corresponding to one of the maximum reflectivities shown in FIG. 2, was used as the monitor light.

Figure 3A:
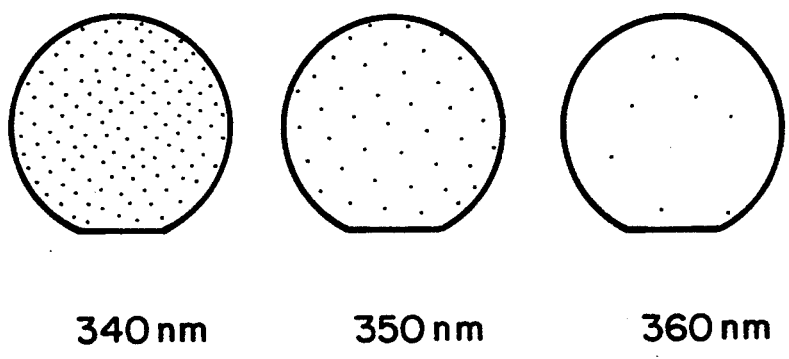
FIGS. 3(a) and 3(b) are views showing the results of foreign matter checking on the surfaces of polysilicon-deposited substrates.

It is understood from FIG. 3(a) that when the monitor light has a wavelength of 755 nm, the number of foreign particles detected greatly varies with changes by $\pm$10 nm in the thickness of the polysilicon layer even though substantially the same number of sample particles are attached, and thus, the sensitivity with which foreign particles can be detected greatly varies.

Figure 3B:
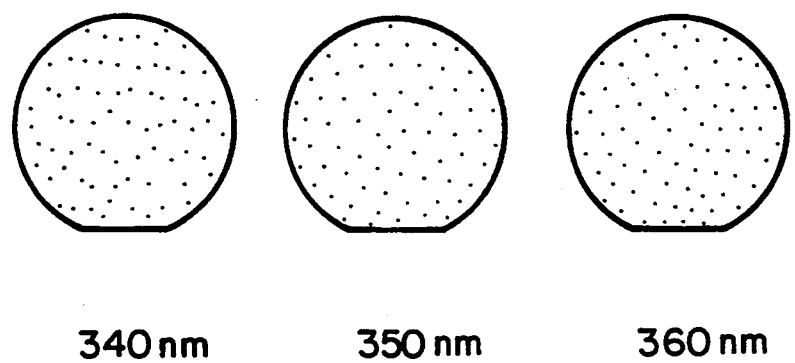

It is understood from FIG. 3(b), however, that when the monitor light has a wavelength of 820 nm, the number of foreign particles detected remains substantially the same in spite of slight changes in the thickness of the polysilicon layer, and thus, the sensitivity of detection can remain stable even when variations have been caused in the thickness of deposited films by a semiconductor process.

As has been described above, with a foreign matter checking apparatus and a foreign matter checking method according to the present invention, the use of light of a wavelength having a maximum reflectivity minimizes the influence of slight variations in the thickness of the deposited film, thereby stabilizing the sensitivity of detection. Furthermore, it is possible to eliminate those deposited-film thickness regions in which the sensitivity of foreign-particle detection with respect to multi-layer thin film substrates deteriorates (the elimination had been difficult in a conventional system using a fixed wavelength), thereby enabling an increase in detection sensitivity to substantially the maximum level. Thus, the present invention makes it possible to perform foreign matter checking with high sensitivity and high precision.

What is claimed is:

1. A method for checking and detecting foreign matter on a substrate, the method comprising:
    (a) measuring a spectrum of reflectivity of the substrate;
    (b) selecting a wavelength at which the reflectivity has a maximum value;
    (c) exposing a portion of the substrate to a monitor light of the wavelength at which the reflectivity has a maximum value so that the foreign matter scatters a portion of the monitor light; and
    (d) detecting the portion of the monitor light which the foreign matter scatters.

2. A method as in claim 1, wherein the substrate comprises a multi-layer structure.

3. A method as in claim 1, wherein the substrate is a semiconductor substrate.

4. A method as in claim 3, wherein the substrate comprises a multi-layer structure.

5. A method as in claim 1, further comprising a step of scanning an entire surface of the substrate with the monitor light.

6. A method as in claim 5, wherein the step of scanning comprises a step of rotating the substrate.

7. A method as in claim 6, wherein the step of rotating the substrate comprises varying a rotational speed at which the substrate is rotated so that a linear velocity of a light spot formed by the monitor light on the substrate is constant.

* * * * *